United States Patent [19]

Sakai et al.

[11] Patent Number: 4,814,495

[45] Date of Patent: Mar. 21, 1989

[54] METHOD FOR THE PREPARATION OF HYDROXYBENZOIC ACID

[75] Inventors: Tsunenori Sakai; Toshio Ishiguro; Takaya Ishihara, all of Tokuyama, Japan

[73] Assignee: Idemitsu Petrochemical Co., Ltd., Tokyo, Japan

[21] Appl. No.: 203,345

[22] Filed: Jun. 6, 1988

[30] Foreign Application Priority Data

Jun. 24, 1987 [JP] Japan .................................. 62-157140
Jun. 26, 1987 [JP] Japan .................................. 62-159097
Oct. 27, 1987 [JP] Japan .................................. 62-269315

[51] Int. Cl.$^4$ ............................................. C07C 51/15
[52] U.S. Cl. ..................................................... 562/424
[58] Field of Search .......................................... 562/424

[56] References Cited

U.S. PATENT DOCUMENTS 4,376,867 3/1983 Jansen et al. ........................ 562/424
4,529,817 7/1985 Stopp et al. ......................... 562/424
4,780,567 10/1988 Ueno et al. .......................... 562/424

FOREIGN PATENT DOCUMENTS 89564 9/1983 European Pat. Off. ............ 562/424
1004347 3/1983 U.S.S.R. ............................... 562/424
1189385 4/1970 United Kingdom ................ 562/424

Primary Examiner—Paul J. Killos
Attorney, Agent, or Firm—Frishauf, Holtz, Goodman & Woodward

[57] ABSTRACT

In the Kolbe-Schmitt process for the preparation of hydroxybenzoic acid by the reaction of potassium phenolate with carbon dioxide gas followed by precipitation of the hydroxybenzoic acid in the mixture acidified with hydrochloric acid, the potassium value in the acidified mother liquor is conventionally recovered by electrolysis after removing the organic impurities by chlorination with chlorine. The disadvantages in the use of chlorine can be dissolved by replacing the chlorine treatment with (a) dehydration of the acidified mother liquor followed by calcination of the dehydrated product, (b) salting-out by blowing hydrogen chloride gas into the acidified mother liquor, or (c) reverse osmosis treatment prior to the electrolysis to convert potassium chloride into potassium hydroxide, for example, by using an ion exchange membrane.

4 Claims, No Drawings

METHOD FOR THE PREPARATION OF HYDROXYBENZOIC ACID

BACKGROUND OF THE INVENTION

The present invention relates to a method for the preparation of hydroxybenzoic acid. More particularly, the invention relates to a method for the preparation of hydroxybenzoic acid, such as 4-hydroxybenzoic acid which is a useful starting material in the manufacture of various chemical products including antiseptic agents, fungicidal agents, high-polymeric liquid crystals, color-developing agents on heat-sensitive recording paper and so on, in which the alkali metal hydroxide used in the reaction can be efficiently recovered in the form suitable for re-use containing little impurities.

As is known, the most conventional prior art method for the preparation of hydroxybenzoic acid is to utilize the socalled Kolbe-Schmitt reaction. In this method, potassium salt of phenol, i.e. potassium phenolate, is heated in the presence of carbon dioxide gas to form hydroxybenzoic acid which is then precipitated in and isolated from the reaction mixture by acidification with hydrochloric acid.

One of the problems in this prior art method is that the mother liquor in the precipitation of the hydroxybenzoic acid by acidification contains potassium chloride which is the reaction product of hydrochloric acid with potassium hydroxide used as one of the starting materials and the potassium chloride contained in the mother liquor can be recovered only with great difficulties because the mother liquor necessarily contains considerable amounts of phenol, hydroxybenzoic acid, by-products and other organic materials.

Needless to say, it is very important from the standpoint of economy in the industrial production of hydroxybenzoic acid by the above described process to recover the potassium chloride from the mother liquor and convert it by electrolysis into potassium hydroxide to be re-used. Several attempts and proposals of course have been made hitherto in this regard but none of them is suitable for industrialization.

For example, Japanese Patent Publication No. 49-48304 teaches a method for the recovery of the potassium component in the above described process, according to which the acidified mother liquor is reacted with chlorine and freed from the thus formed hardly soluble or insoluble chlorinated compounds followed by electrolysis. This method, however, has several disadvantages that the use of toxic and corrosive chlorine necessarily causes problems in the workers' safety and corrosion of apparatuses, that the chlorinated compounds produced by the reaction of chlorine also have toxicity and that sufficiently high recovery of the potassium component can hardly be obtained. Therefore, this method has only a very limited practical value.

SUMMARY OF THE INVENTION

The present invention accordingly has an object to provide a novel method for the preparation of hydroxybenzoic acid free from the above described problems and disadvantages in the prior art methods, in which the alkali metal value contained in the mother liquor in the precipitation of hydroxybenzoic acid can be efficiently recovered in the form of an alkali metal hydroxide, such as potassium hydroxide, of high purity without using toxic and corrosive chlorine.

The method of the present invention, established as a result of the extensive investigations undertaken with the above mentioned object, is based on principle that, in the manufacturing process of hydroxybenzoic acid by the Kolbe-Schmitt reaction, the acidified mother liquor after separation of the precipitated hydroxybenzoic acid is subjected to a specific post-treatment to isolate the alkali metal salt which is then electrolyzed into an alkali metal hydroxide having high purity.

Thus, the method of the present invention for the preparation of hydroxybenzoic acid comprises, following a process in which an alkali metal phenolate formed by the reaction of phenol and an alkali metal hydroxide is reacted with carbon dioxide gas, the reaction product obtained thereby is dissolved in water, the resultant aqueous solution is acidified by adding an inorganic acid to precipitate the hydroxybenzoic acid, and the thus precipitated hydroxybenzoic acid is separated from the mother liquor, the steps of:

(A) subjecting the acidified mother liquor to a treatment selected from the group consisting of
 (a) a dehydration treatment of the mother liquor followed by calcination of the resultant dehydrated product
 (b) a salting-out treatment by blowing hydrogen chloride gas thereinto, and
 (c) a reverse osmosis treatment, to isolate the alkali metal salt contained in the mother liquor;

(B) subjecting the alkali metal salt to electrolysis to form an alkali metal hydroxide; and (C) recovering and using the alkali metal hydroxide in the reaction with phenol.

DETAILED DESCRIPTION OF THE PREFERRED EMBODIMENTS

In the method of the present invention, phenol is reacted with an alkali metal hydroxide to form an alkali metal phenolate which is then reacted with carbon dioxide gas to give a reaction product containing an alkali metal salt of hydroxybenzoic acid. The reaction product is dissolved in water to give an aqueous solution which is then freed from unreacted phenol by solvent extraction followed by acidification with addition of an inorganic acid so as to precipitate the desired hydroxybenzoic acid. The precipitated hydroxybenzoic acid is separated from the acidified mother liquor by solid-liquid separation. The above described procedure can be performed according to a known method.

The reaction of phenol and an alkali metal hydroxide is usually performed by mixing 1 mole of phenol with 0.1 to 10 moles or, preferably, 0.5 to 2 moles of the alkali metal hydroxide and effecting the reaction in the mixture at a temperature in the range from $-10°$ C. to $+200°$ C. or, preferably, from $15°$ C. to $100°$ C. The reaction can be complete almost instantaneously as the reactants are mixed together or can proceed over a period of 0.01 to 10 hours.

The alkali metal hydroxide used in the reaction with phenol includes sodium hydroxide and potassium hydroxide. When the desired hydroxybenzoic acid is 4-hydroxybenzoic acid, the alkali metal hydroxide is preferably potassium hydroxide. It is optional to use sodium and potassium hydroxides in combination according to need.

Although the reaction of phenol and an alkali metal hydroxide can proceed in an anhydrous condition, the reaction is preferably performed in the presence of water as a solvent. When used, the amount of water is usually in the range up to 80% by weight or, preferably, from 5 to 50% by weight based on the overall amount of the reaction mixture. Usually, quite satisfactory results can be obtained by using the alkali metal hydroxide recovered in the above mentioned step (C) in the form of an aqueous solution to utilize the water therein as the solvent instead of using fresh water to dissolve anhydrous phenol and alkali metal hydroxide.

Apart from the water used as the solvent in the reaction, water is also produced by the reaction of phenol and the alkali metal hydroxide. In order to obtain the alkali metal phenolate in a substantially anhydrous condition, the reaction mixture after completion of the reaction is distilled to remove the water, if necessary, together with the unreacted phenol although the thus obtained anhydrous alkali metal phenolate may contain free alkali metal hydroxide and/or phenol.

The alkali metal phenolate is then reacted with carbon dioxide gas by heating according to a conventional procedure to give a reaction mixture containing the hydroxybenzoic acid in the form of an alkali metal salt. The reaction can be performed while the unreacted phenol or by-product phenol is under distilling off. It is preferable, however, to perform the reaction in the presence of free phenol. When the alkali metal phenolate subjected to the reaction contains unreacted alkali metal hydroxide, in particular, it is preferable that the reaction mixture contains free phenol at least in a molar amount to balance the alkali metal hydroxide. The presence of free phenol is effective not only to convert the alkali metal hydroxide into the alkali metal phenolate but also to increase the efficiency of the reaction between the phenolate and carbon dioxide gas. If desired, the reaction mixture may be admixed with an organic solvent so that the efficiency of the reaction can be further increased.

The reaction of the alkali metal phenolate and carbon dioxide gas is performed usually at a temperature in the range from 100° to 300° C. or, preferably, from 160° to 260° C. with supply of, per mole of the alkali metal phenolate, from 0.1 to 100 moles or, preferably, from 0.5 to 50 moles of carbon dioxide gas under a pressure up to 100 kg/cm$^2$ or, preferably, up to 50 kg/cm$^2$. The reaction is complete usually within 0.001 to 10 hours or, in most cases, within 0.1 to 5 hours. The amount of free phenol contained in the reaction mixture, which is at least to balance the alkali metal hydroxide as is mentioned above, should not exceed 50 moles or, preferably, be in the range from 0.1 to 10 moles per mole of the alkali metal phenolate. The amount of the organic solvent, when used, should not exceed 5000 g or, preferably, 2000 g per mole of the alkali metal hydroxide.

The organic solvent used here should be immiscible with water in order to facilitate the subsequent procedure for the separation of precipitated hydroxybenzoic acid from the mother liquor. Suitable organic solvents in this regard include hydrocarbon solvents such as gas oil, kerosine, benzene, toluene, xylene and the like and ether solvents such as diethyl ether, dipropyl ether and the like.

The thus obtained reaction product contains the unreacted or by-product phenol together with, when used, the organic solvent. Accordingly, the reaction product is dissolved in water to give an aqueous solution which is freed therefrom and acidified. Following is a typical procedure for the removal of the free phenol and preparation of the aqueous solution.

When the reaction of the alkali metal phenolate and carbon dioxide is performed with admixture of the reaction mixture with an organic solvent, for example, 2 to 100 parts by weight or, preferably, 5 to 50 parts by weight of water are added to 100 parts by weight of the reaction mixture after completion of the reaction and the mixture is subjected to phase separation into the aqueous phase and the organic phase which is mainly the organic solvent used in the reaction. The aqueous solution thus obtained is then admixed with 1 to 500 parts by weight or, preferably, 5 to 100 parts by weight of an extractant per 100 parts by weight of the reaction mixture after completion of the reaction to extract the organophilic materials in the aqueous solution such as the free phenol and the like by agitating the mixture for 0.1 to 60 minutes at a temperature in the range from −10° to 130° C. or, preferably, from 10 to 100° C followed by phase separation into the aqueous phase and the extractant phase. When no organic solvent is used in the reaction, the reaction mixture after completion of the reaction is also admixed with water and an extractant to extract the free phenol and the like into the extractant under about the same conditions as above followed by phase separation into the aqueous phase and the extractant phase.

The above described process of extraction is effective to efficiently remove the free phenol from the reaction mixture leaving the alkali metal salt of hydroxybenzoic acid in the aqueous solution.

The above mentioned extractant is not particularly limitative and any of conventionally used water-insoluble organic solvents can be used successfully including benzene, toluene, xylene, ether and the like.

The aqueous solution obtained in this manner is then acidified according to a conventional method by the addition of an inorganic acid to precipitate the hydroxybenzoic acid which is separated from the mother liquor. The inorganic acid used here may be hydrochloric acid, sulfuric acid, nitric acid and the like, of which hydrochloric acid is preferred. The inorganic acid is added to the aqueous solution as an aqueous solution of a concentration in the range from 1 to 80% by weight. The amount of the inorganic acid added to the aqueous solution is in the range from 0.1 to 500 parts by weight per 100 parts by weight of the aqueous solution. For example, it is preferable to add from 10 to 500 parts by weight of a hydrochloric acid of 1 to 36% by weight concentration to 100 parts by weight of the aqueous solution.

The hydroxybenzoic acid is precipitated by this acidification treatment and can be separated from the mother liquor by a suitable solid-liquid separation method such as filtration and centrifugation. The mother liquor freed from the hydroxybenzoic acid as the desired product contains the alkali metal component to be recovered.

In the method of the present invention, the alkali metal component contained in the acidified mother liquor is recovered and converted into an alkali metal hydroxide to be re-used. The recovery of the alkali metal component from the mother liquor is performed in one of the following treatment procedures including:

(a) a dehydration treatment of the mother liquor followed by calcination of the dehydrated product;

(b) a salting-out treatment by blowing hydrogen chloride gas into the mother liquor; and (c) a reverse osmosis treatment.

In the next place, the thus obtained alkali metal salt such as potassium chloride is subjected to electrolysis to be converted into hydroxide of the alkali metal, e.g., potassium hydroxide.

In the above mentioned treatment (a), the mother liquor is partially dehydrated and the alkali metal salt still in the form of a wet cake is then calcined. The alkali metal salt in the form of a wet cake contains unreacted phenol, hydroxybenzoic acid, by-products and other organic matter and these impurities can be removed by calcining the wet cake. The calcination treatment is performed at a temperature in the range from 200° to 1000° C. or, preferably, from 400° to 800° C. for a length of time in the range from 0.01 to 10 hours or, preferably, from 0.1 to 5 hours. This calcination treatment may be performed by using flames.

Alternatively, the acidified mother liquor containing the alkali metal salt is added to the aqueous solution of the alkali metal salt of hydroxybenzoic acid before acidification followed by partial dehydration therefrom and the precipitated alkali metal salt is separated from the liquid and subjected to the calcination treatment under substantially the same conditions as described above.

In the treatment (b) mentioned above, hydrogen chloride gas is blown into the mother liquor so that the alkali metal component in the mother liquor is precipitated in the form of a chloride. For example, hydrogen chloride gas is blown into the mother liquor in an amount from 0.5 to 25 g per 100 ml of the mother liquor kept at a temperature in the range from 0° to 100° C. or preferably, from 20° to 80° C.

The reverse osmosis as the treatment (c) can be performed according to a known procedure at a temperature in the range from 0° to 100° C. or, preferably, from 10° to 45° C. by use of a semipermeable membrane for reverse osmosis such as membranes of cellulose acetate, aromatic polyamide and the like. If desired, the velocity of permeation through the membrane can be increased by pressure.

In a typical embodiment of the reverse osmosis treatment, the acidified mother liquor stored in a reservoir is continuously introduced by means of a pump into the feed zone of a reverse-osmosis vessel so that an aqueous solution containing the alkali metal salt alone is separated from the mother liquor partly and transferred through the membrane into the separation zone, the rest being recycled to the reservoir. In this manner, an aqueous solution containing the alkali metal salt alone can be continuously taken out of the separation zone. The type of the apparatus for practicing the reverse osmosis treatment is not particularly limitative including plane-membrane type, spiral type, tubular type, hollow filament type and the like. The aqueous solution of the alkali metal salt obtained in this manner from the acidified mother liquor by the reverse osmosis treatment usually has a controlled concentration of 12 to 36% by weight.

The alkali metal salt obtained in the above described manner is then converted to an alkali metal hydroxide by electrolysis. One of the satisfactory methods for the electrolysis is the conventional method by using an ion-exchange membrane. A Naphion membrane works satisfactorily as the ion-exchange membrane in most cases. Suitable materials for the anode and cathode are carbon and platinum, respectively. The electrolysis is performed preferably under the conditions including the current density on the cathode of 10 to 50 A/dm$^2$, cell voltage of 1 to 5 volts/cell and temperature of the electrolyte solution in the range from 0° to 100° C.

In this manner, an aqueous solution of the alkali metal hydroxide, e.g., potassium hydroxide, is obtained in a high concentration in the cathode cell. The aqueous solution of the alkali metal hydroxide is recycled and re-used in the reaction with phenol either as such or after concentration by evaporating at least a part of water according to need. The chlorine produced at the anode can of course be used in various applications in a usual way.

As is understood from the description given above, the present invention provides a very advantageous process for the industrial production of hydroxybenzoic acid because the alkali metal component used in the process can be recovered in a good yield as an alkali metal hydroxide of high purity without using any material having toxicity or corrosiveness. The hydroxybenzoic acid prepared according to the inventive method can of course be used in a wide fields of applications as a starting material for the syntheses of various valuable organic compounds including antiseptic agents, fungicidal agents, high-polymeric liquid crystals, color-developing agents on heat-sensitive recording paper and so on in just the same manner as in the use of hydroxybenzoic acid products produced in conventional methods.

In the following, the method of the present invention is described in more detail by way of examples and comparative examples.

EXAMPLE 1

Into an autoclave of 1 liter capacity equipped with a stirrer were introduced 57.66 g of a 50% by weight aqueous solution of potassium hydroxide and 53.46 g of phenol and the mixture was heated at 150° to 200° C. with agitation under a reduced pressure of 5 to 10 mmHg so that water and unreacted phenol were completely removed by distilling off to give 68.08 g of potassium phenolate. Thereafter, 272.22 g of gas oil and 33.96 g of phenol were introduced into the autoclave released to the atmospheric air and the autoclave was flushed with nitrogen gas. The mixture in the autoclave was then heated with agitation in the nitrogen atmosphere and, when the temperature had reached 230° C., pressurized by introducing carbon dioxide gas up to a pressure of 5 kg/cm$^2$ to continue agitation for 10 minutes by keeping the temperature at 230° C.

After completion of the above mentioned reaction time, the autoclave was cooled to 80° C. and the mixture in the autoclave with admixture of 140 ml of water was transferred into a separatory funnel of 1 liter capacity where the mixture was separated into the aqueous layer and the gas oil layer. The aqueous phase discharged out of the separatory funnel was scrubbed three times each with 50 ml of toluene to extract unreacted phenol.

The aqueous solution after the above mentioned extraction treatment was then acidified by adding 44.3 ml of concentrated hydrochloric acid and the crystalline precipitates were collected by filtration to give 230 g of an acidified other liquor. The precipitates as collected were composed of 37.1 g of 4-hydroxybenzoic acid and 0.71 g of salicylic acid.

The above obtained mother liquor contained 2.5% by weight of phenol, 0.4% by weight of 4-hydroxybenzoic acid, 0.3% by weight of salicylic acid and 16.6% by weight of potassium chloride.

The mother liquor was subjected to partial evaporation of water to give 52.0 g of a wet cake of potassium chloride in which the above mentioned organic impurities such as phenol were contained.

The wet potassium chloride was calcined in a furnace at 700° C. for 5 hours to give 38.3 g of a calcined material.

The potassium chloride obtained in this manner was dissolved in 106 ml of water and the aqueous solution was subjected to electrolysis to recover potassium hydroxide. The electrolysis was performed with a carbon anode and a platinum cathode separated with a membrane of Naphion as the ion exchange membrane at an electrolyte bath temperature of 80° C. The current density was 30 A/dm$^2$ on the cathode and the voltage was 4.2 volts/cell. Potassium hydroxide could be recovered in a yield of 98%.

EXAMPLE 2

A 230 g portion of the acidified mother liquor obtained under the same conditions as in Example 1 was added to the aqueous solution obtained by phase separation of the reaction mixture of the potassium phenolate and carbon dioxide gas into the gas oil phase and aqueous phase, which contained 25.2 g of potassium 4-hydroxybenzoate and 28.0 g of dipotassium 4-hydroxybenzoate, and neutralized with 13.7 g of a 35% hydrochloric acid followed by heating at 100° C.

Thereafter, 310 g of water were removed by distillation from the aqueous solution so that the concentration of the aqueous solution of potassium 4-hydroxybenzoate was increased to 30% by weight. The aqueous solution was cooled to 20° C. and the precipitates of potassium chloride were collected by filtration and washed with a small volume of water.

The wet cake of potassium chloride was calcined in a furnace at 700° C. for 5 hours to give 27.2 g of a calcined material.

The thus obtained potassium chloride was dissolved in 75 ml of water and the aqueous solution was subjected to electrolysis under the same conditions as in the preceding example to recover potassium hydroxide in a yield of 71%.

COMPARATIVE EXAMPLE 1

A mixture composed of 386 g of phenol and 472 g of a 50% potassium hydroxide in an autoclave equipped with a stirrer was heated with agitation at a temperature of 100° to 150° C. under a reduced pressure of 10 to 15 mmHg to remove water and unreacted phenol completely by distillation. Carbon dioxide gas was then introduced into the autoclave after releasing to the atmospheric air and reacted with the mixture in the autoclave kept at 200° to 230° C. for about 1 hour followed by further reduction of the pressure to remove the phenol produced as a by-product by distillation.

After removing the by-product phenol in an overall amount of about 190 g by repeating this procedure with distillation three times, 448 g of the thus obtained reaction product were dissolved in 1000 g of water and the aqueous solution after decoloration by use of activated charcoal and zinc dust was admixed with 350 g of a 35% hydrochloric acid to have a pH of 3.0. The precipitates of 4-hydroxybenzoic acid in the thus acidified mixture were collected by filtration. The yield of the 4-hydroxybenzoic acid was 270 g corresponding to 95% of the theoretical value and the purity thereof was 99.5%. The amount of the mother liquor after separation of the precipitates was 1500 g, which contained 0.4% of 4-hydroxybenzoic acid, 0.2% of salicylic acid and 20.0% of potassium chloride as well as iron, zinc and the like each in a trace amount.

A 1000 g portion of the acidified mother liquor was taken in a flask equipped with a stirrer and a reflux condenser and chlorine gas was blown thereinto at 70° C. so that a reaction took place to give a chlorinated product which was removed from the bottom portion of the flask as it was formed. The overall amount of chlorine gas absorbed in the mother liquor was about 26 g after 3 hours from the start of the reaction when the reaction was complete. The reaction mixture was cooled to 30° C. and freed from the remaining chlorinated product and then 45 g of a 50% potassium hydroxide were added thereto to form precipitates in the mixture, which were collected by filtration. The overall amount of the chlorinated product removed from the mixture was about 15 g as dried.

The thus obtained aqueous solution of potassium chloride was subjected to electrolysis at a temperature of the electrolyte solution of 70° C. by using carbon and mercury as the anode and cathode, respectively, under the conditions of the current density on the cathode of 30 A/dm$^2$, cell voltage of 4.2 volts and amalgam concentration of 0.2%. The thus obtained amalgam was decomposed with an appropriate amount of water to recover potassium hydroxide in 50% concentration. The yield of the recovered potassium hydroxide was 70%.

EXAMPLE 3

An acidified mother liquor was obtained in substantially the same manner as in Example 1 except that the reaction of phenol and potassium hydroxide was performed by heating the reaction mixture at 100° to 150° C. under a reduced pressure of 10 to 15 mmHg.

Hydrogen chloride gas was blown into the thus obtained mother liquor until the concentration of hydrogen chloride therein had reached 36% and the mother liquor was kept standing at 25° C. for 1 hour so that precipitates of potassium chloride were obtained in an amount of 33.4 g.

The precipitates collected by filtration were rinsed with a small volume of water and then subjected to electrolysis in the same manner as in Example 1 to recover potassium hydroxide. The yield of the recovered potassium hydroxide was 87%.

EXAMPLE 4

An acidified mother liquor was obtained in substantially the same manner as in Example 1 except that the reaction of phenol and potassium hydroxide was performed by heating the reaction mixture at 100° to 150° C. under a reduced pressure of 10 to 15 mmHg.

The mother liquor was subjected to a reverse osmosis treatment by use of an apparatus having a composite semipermeable membrane of a crosslinked polyamide type with a thickness of 30 nm (SU-210S, a product by Toray, Inc.). Potassium chloride and organic materials were eliminated from the mother liquor by this treatment in proportions of about 5% and almost 100%, respectively.

The mother liquor was then subjected to electrolysis in the same manner as in Example 1 to recover potassium hydroxide in a yield of 99%.

What is claimed is:

1. A method for the preparation of hydroxybenzoic acid which comprises, following a process in which an alkali metal phenolate formed by the reaction of phenol and an alkali metal hydroxide is reacted with carbon dioxide gas, the reaction product obtained thereby is dissolved in water, the aqueous solution is acidified by adding an inorganic acid to precipitate the hydroxybenzoic acid, and the thus precipitated hydroxybenzoic acid is separated from the mother liquor, the steps of:

(A) subjecting the acidified mother liquor to a treatment selected from the group consisting of
  (a) a dehydration treatment of the mother liquor followed by calcination of the dehydrated product,
  (b) a salting-out treatment by blowing hydrogen chloride gas into the mother liquor, and
  (c) a reverse osmosis treatment,
to isolate the alkali metal salt contained in the mother liquor;

(B) subjecting the alkali metal salt to electrolysis to form an alkali metal hydroxide; and (C) recovering the alkali metal hydroxide and using the recovered alkali metal hydroxide in the reaction with phenol.

2. The method for the preparation of hydroxybenzoic acid as claimed in claim 1 wherein the alkali metal hydroxide is potassium hydroxide.

3. The method for the preparation of hydroxybenzoic acid as claimed in claim 1 wherein the inorganic acid is hydrochloric acid.

4. The method for the preparation of hydroxybenzoic acid as claimed in claim 1 wherein the electrolysis of the alkali metal salt is performed by using an ion exchange membrane.

* * * * *